United States Patent
Kikuchi et al.

(10) Patent No.: US 12,352,778 B2
(45) Date of Patent: Jul. 8, 2025

(54) FLOW VELOCITY DETERMINING APPARATUS

(71) Applicants: AIR WATER BIODESIGN INC., Kobe (JP); NIKKISO COMPANY LIMITED, Tokyo (JP)

(72) Inventors: Ikuya Kikuchi, Kawagoe (JP); Atsuya Ito, Kawagoe (JP); Ryohei Kagawa, Kawagoe (JP)

(73) Assignees: AIR WATER BIODESIGN INC., Kobe (JP); NIKKISO COMPANY LIMITED, Tokyo (JP)

( * ) Notice: Subject to any disclaimer, the term of this patent is extended or adjusted under 35 U.S.C. 154(b) by 1015 days.

(21) Appl. No.: 17/426,529

(22) PCT Filed: Jan. 31, 2019

(86) PCT No.: PCT/JP2019/003437
§ 371 (c)(1),
(2) Date: Jul. 28, 2021

(87) PCT Pub. No.: WO2020/157926
PCT Pub. Date: Aug. 6, 2020

(65) Prior Publication Data
US 2022/0099696 A1 Mar. 31, 2022

(51) Int. Cl.
*G01P 5/20* (2006.01)
*G01N 15/14* (2006.01)

(52) U.S. Cl.
CPC ............ *G01P 5/20* (2013.01); *G01N 15/1459* (2013.01)

(58) Field of Classification Search
None
See application file for complete search history.

(56) References Cited

U.S. PATENT DOCUMENTS

| 5,106,184 A | 4/1992 | Milbocker |
| 6,211,955 B1 | 4/2001 | Basigi et al. |

(Continued)

FOREIGN PATENT DOCUMENTS

| CN | 1279394 A | 1/2001 |
| CN | 102565002 A | 7/2012 |

(Continued)

OTHER PUBLICATIONS

Notice to Grant a Patent for Invention received in CN 201980090608.9, dated Sep. 30, 2024, in 5 pages.

(Continued)

*Primary Examiner* — Hovhannes Baghdasaryan
(74) *Attorney, Agent, or Firm* — Procopio, Cory, Hargreaves & Savitch LLP

(57) ABSTRACT

A flow velocity determining apparatus (10) includes an irradiating unit (20) that emits irradiation light (L1) toward a liquid mixture (BL) which contains a non-spherical solid (BC) and a liquid (BP) and flows through a flow path (TB), a detecting unit (30) that detects reflected light (L2) emitted by the irradiating unit (20) and reflected by the liquid mixture (BL) flowing through the flow path (TB), the detecting unit (32) being disposed on at least one side of an optical axis (L2A) of the reflected light (L2) when seen in a plan view of an imaginary plane including an optical axis (L1A) of the irradiation light (L1) and the optical axis (L2A) of the reflected light (L2), and a determining unit (40) that determines a flow velocity of the liquid mixture (BL) by using a light amount of the reflected light (L2) detected by the detecting unit (32).

4 Claims, 18 Drawing Sheets

(56) References Cited

U.S. PATENT DOCUMENTS

| | | |
|---|---|---|
| 8,692,982 B2 | 4/2014 | Yoshioka et al. |
| 9,237,856 B2 | 1/2016 | Tateishi et al. |
| 10,352,853 B2 | 7/2019 | Shiono et al. |
| 10,557,937 B2 | 2/2020 | Ando et al. |
| 10,801,831 B2 | 10/2020 | Aizawa et al. |
| 10,856,751 B2 | 12/2020 | Watanabe et al. |
| 2010/0220312 A1 | 9/2010 | Iwai et al. |
| 2011/0199603 A1 | 8/2011 | Yoshioka et al. |
| 2011/0285984 A1 | 11/2011 | Christian et al. |
| 2013/0016335 A1 | 1/2013 | Lo et al. |
| 2013/0090564 A1 | 4/2013 | Tateishi et al. |
| 2015/0025834 A1 | 1/2015 | Ando et al. |
| 2018/0008152 A1 | 1/2018 | Watanabe et al. |
| 2019/0017932 A1 | 1/2019 | Shiono et al. |
| 2019/0094009 A1 | 3/2019 | Aizawa et al. |
| 2020/0205677 A1* | 7/2020 | Ito .................. A61B 5/7257 |
| 2020/0359938 A1* | 11/2020 | Iinaga ............... A61B 5/6824 |

FOREIGN PATENT DOCUMENTS

| | | |
|---|---|---|
| CN | 104126126 A | 10/2014 |
| CN | 104168823 A | 11/2014 |
| CN | 107260155 A | 10/2017 |
| CN | 107389786 A | 11/2017 |
| CN | 108882882 A | 11/2018 |
| CN | 109247945 A | 1/2019 |
| JP | H02-259576 A | 10/1990 |
| JP | H05273225 A | 10/1993 |
| JP | H1085195 A | 4/1998 |
| JP | 2004506919 A | 3/2004 |
| JP | 2007033306 A | 2/2007 |
| WO | 2016092681 A1 | 6/2016 |
| WO | 2011099433 A1 | 8/2018 |

OTHER PUBLICATIONS

International Search Report mailed on Mar. 12, 2019 from International Application No. PCT/JP2019/003437, 2 pages.

Office Action received in CN 201980090608.9, dated Nov. 28, 2023, in 14 pages total (with translation).

Extended European Search Report in the corresponding European patent application 19912577.4-1001 / 3919919, which was sent on Aug. 4, 2022. 8 Pages.

* cited by examiner

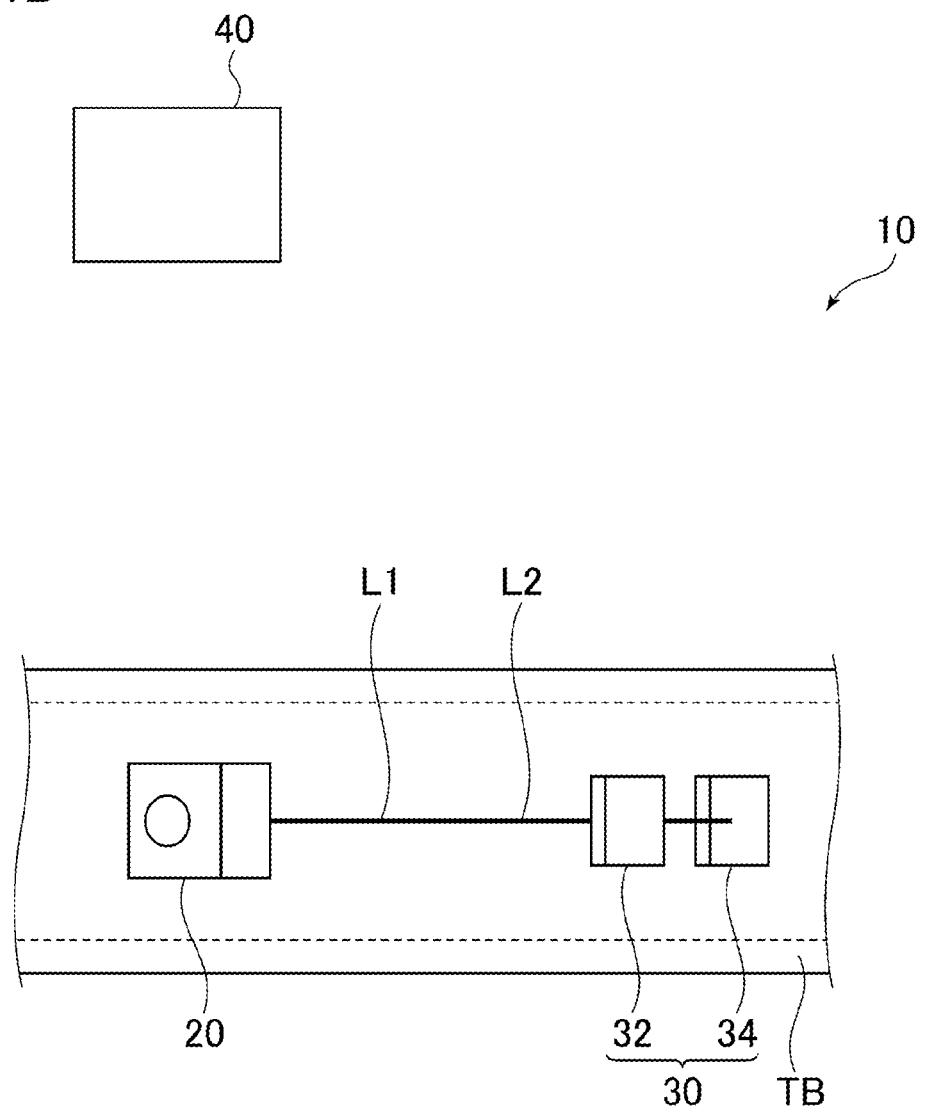

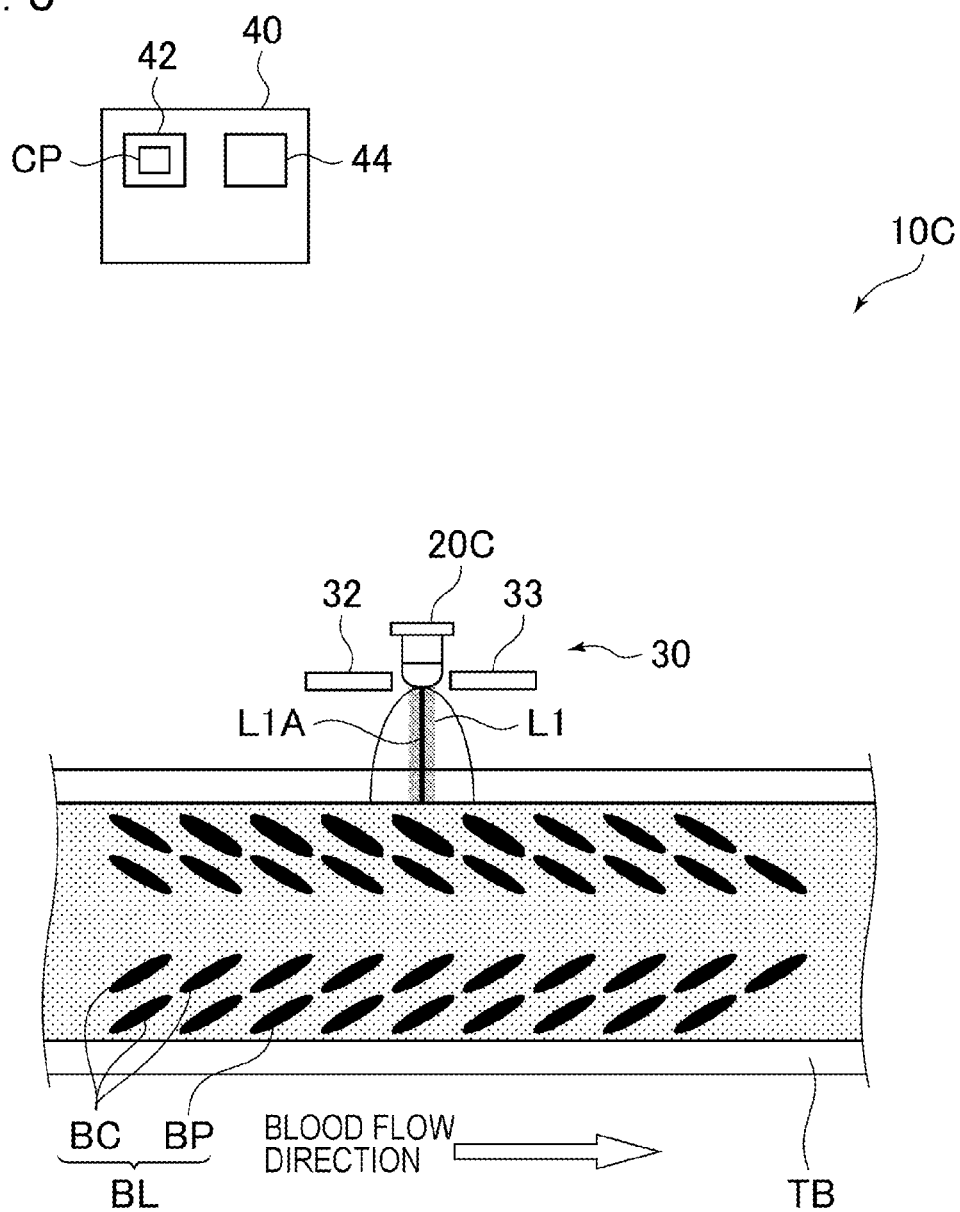

FLOW VELOCITY DETERMINING APPARATUS

CROSS-REFERENCE TO RELATED APPLICATIONS

This application is a U.S. National Stage entry of PCT Application No: PCT/JP2019/003437 filed Jan. 31, 2019, the contents of which are incorporated herein by reference.

TECHNICAL FIELD

The present invention relates to a flow velocity determining apparatus.

BACKGROUND ART

Patent Document 1 discloses a laser blood flowmeter that calculates a scalar quantity of a blood flow velocity at a desired part of a tissue at any depth under an epidermis of a living body and a three-dimensional flow velocity direction of a blood flow from the epidermis of the living body in a non-invasive and real-time manner to measure an absolute value of a blood flow rate and the blood flow direction in a desired measurement region in a real-time manner.

The laser blood flowmeter emits a pair of two laser beams from a laser light source and performs calculation processing of electric signals from a photoelectric sensor that observes interference waves generated in the measurement region by signal processing means, repeatedly. Therefore, the laser blood flowmeter sequentially calculates the blood flow velocity and the blood flow direction by sequentially calculating the blood flow velocity in each of the three orthogonal directions.

RELATED DOCUMENT

Patent Document

[Patent Document 1] Japanese Published Patent Application A-H10-085195

SUMMARY OF THE INVENTION

Technical Problem

The laser blood flowmeter disclosed in Patent Document 1 can calculate the blood flow velocity and the blood flow direction of blood, but the configuration thereof is not simple.

An object to be solved by the present invention is, for example, to provide a flow velocity determining apparatus capable of determining, with a simple configuration, the flow velocity of a liquid mixture which contains a non-spherical solid and a liquid and flows through a flow path.

Solution to Problem

The invention according to claim 1 relates to a flow velocity determining apparatus including an irradiating unit that emits irradiation light toward a liquid mixture which contains a non-spherical solid and a liquid and flows through a flow path, a detecting unit that detects reflected light emitted by the irradiating unit and reflected by the liquid mixture flowing through the flow path, the detecting unit being disposed on at least one side of an optical axis of the reflected light when seen in a plan view of an imaginary plane including an optical axis of the irradiation light and the optical axis of the reflected light, and a determining unit that determines a flow velocity of the liquid mixture by using a light amount of the reflected light detected by the detecting unit.

The object described above, other objects, features, and advantages will be further clarified by the preferred embodiments described below and the accompanying drawings.

BRIEF DESCRIPTION OF THE DRAWINGS

FIG. 1B is a top view of the flow velocity determining apparatus and the tube in the state of FIG. 1A.

FIG. 8 is a diagram showing a flow velocity determining apparatus of a third embodiment, and is a vertical cross-sectional view in a state in which the flow velocity determining apparatus is set in a tube.

DESCRIPTION OF EMBODIMENTS

Overview

Figure 1A:
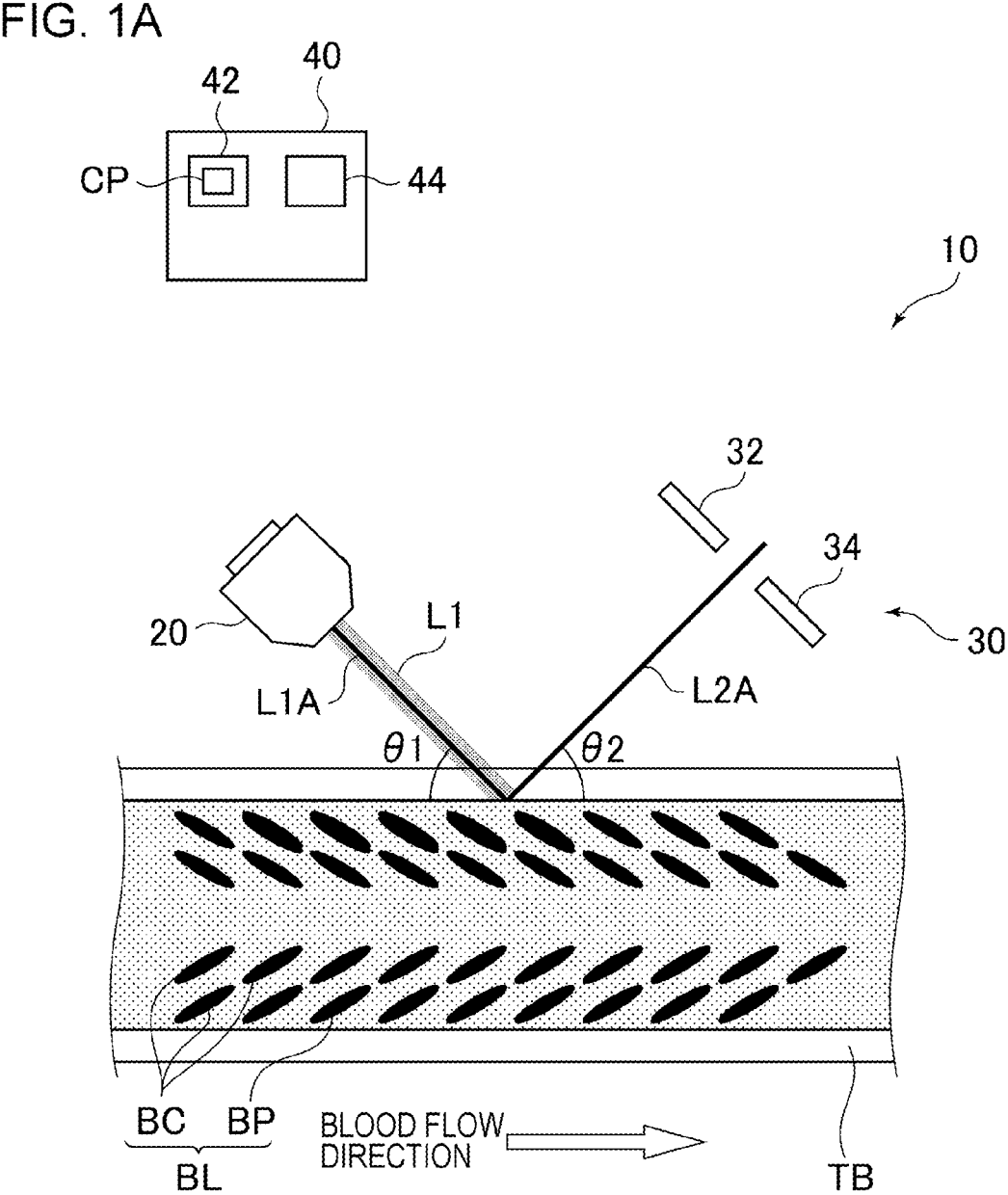
FIG. 1A is a diagram showing a flow velocity determining apparatus of a first embodiment, and is a vertical cross-sectional view in a state in which the flow velocity determining apparatus is set in a tube.

Hereinafter, first, second, and third embodiments of the present invention will be described with reference to the drawings. Then, modification examples of the embodiments will be described with reference to the drawings. In all the drawings to be referred to, the components having the same function are designated by the same reference numerals, and the description thereof will not be repeated in the specification.

First Embodiment

The first embodiment will be described below. First, a function and a configuration of a flow velocity determining apparatus 10 of the present embodiment will be described with reference to FIGS. 1A and 1B, and the like. Then, a flow velocity determining operation of blood BL (an example of a liquid mixture, see FIG. 1A and the like) by the flow velocity determining apparatus 10 of the present embodiment will be described with reference to FIGS. 3A and 3B, and the like. Effects of the present embodiment will be described in the description of the flow velocity determining operation of the blood BL.

<Function and Configuration of First Embodiment>

FIG. 1A is a diagram showing the flow velocity determining apparatus 10 of the present embodiment, and is a vertical cross-sectional view in a state in which the flow velocity determining apparatus 10 is set in a tube TB (an example of a flow path). FIG. 1B is a top view of the flow velocity determining apparatus 10 and the tube TB in the state of FIG. 1A.

The flow velocity determining apparatus 10 of the present embodiment has a function of detecting light (reflected light L2) that is emitted to the blood BL that flows through the tube TB and reflected by the blood BL, and determining a flow velocity of the blood BL by using a light amount of the detected reflected light L2.

The flow velocity determining apparatus 10 of the present embodiment includes an irradiating unit 20, a detecting unit 30, and a control unit 40 (an example of a determining unit).

[Blood and Flow Path]

Here, the blood BL and the tube TB are not the components of the flow velocity determining apparatus 10 of the present embodiment. However, the flow velocity of the blood BL is a determining target of the flow velocity determining apparatus 10 of the present embodiment, and the tube TB is used as a member that allows the blood BL to flow in a case in which the flow velocity of the blood BL is determined (measured) by the flow velocity determining apparatus 10. Before describing each component of the flow velocity determining apparatus 10 of the present embodiment, the blood BL and the tube TB will be described.

The blood BL includes red blood cells BC (an example of a non-spherical solid) and blood plasma BP (an example of a liquid) (see FIGS. 1A, 3A to 3C, and the like). As an example, the tube TB is made of a material capable of transmitting the light (irradiation light L1) emitted by the irradiating unit 20, and is used as a tube that allows the blood BL to flow (see FIGS. 3A to 3C). As an example, the shape of the red blood cell BC is a disk shape in which a diameter is 7 μm to 8 μm, a thickness is 1 μm to 2 μm, and the peripheral portion thereof is thicker than the inner portion, and it is regarded as an example of the non-spherical solid.

[Irradiating Unit]

As an example, the irradiating unit 20 is used as a laser light source, and has a function of irradiating the blood BL that flows through the tube TB with coherent light (irradiation light L1) as shown in FIG. 1A. The irradiating unit 20 is disposed such that the irradiation light L1 emitted by the irradiating unit 20 itself has an optical axis L1A in a diagonal direction with respect to the tube TB, that is, the blood BL that flows through the tube TB. In the present embodiment, an angle of the optical axis L1A with respect to the tube TB is defined as an angle θ1 (45° as an example).

[Detecting Unit]

The detecting unit 30 has a function of detecting the light (reflected light L2) emitted by the irradiating unit 20 and reflected by the blood BL that flows through the tube TB. As shown in FIG. 1A, the detecting unit 30 of the present embodiment includes a first detecting unit 32 disposed on one side of an optical axis L2A of the reflected light L2 and a second detecting unit 34 disposed on the other side. Here, in a case in which an angle of the optical axis L2A with respect to the tube TB is defined as an angle θ2, the angle θ2 is −45°, that is, −θ1.

Further, it can be said that FIG. 1A is a plan view of an imaginary plane (not shown) including the optical axis L1A and the optical axis L2A (a view seen from a direction orthogonal to the imaginary plane). Then, as shown in FIG. 1A, the first detecting unit 32 and the second detecting unit 34 are disposed respectively on one side and the other side (both sides) of the optical axis L2A when seen in a plan view of the imaginary plane (not shown) including the optical axis L1A and the optical axis L2A. The optical axis L2A in this case is the optical axis in a case in which the blood BL in the tube TB does not flow. Stated another way, in the present embodiment, the first detecting unit 32 and the second detecting unit 34 have a relationship that is disposed line-symmetrically with the optical axis L2A by using the optical axis L2A in a case in which the blood BL in the tube TB does not flow as a line of symmetry.

The first detecting unit 32 and the second detecting unit 34 each detect the light reflected by the blood BL at the time of the blood flow velocity determining operation of the blood BL, which will be described below, and then transmit detection signals to the control unit 40.

[Control Unit]

The control unit 40 has a function of controlling the irradiating unit 20 and the detecting unit 30 and a function of receiving the detection signals transmitted from the first detecting unit 32 and the second detecting unit of the detecting unit 30 to determine the blood flow direction (flow direction), flow velocity, and the like of the blood BL. A storage device 42 of the control unit 40 accommodates a measurement program CP for exerting the latter function.

The specific function of the control unit 40 will be described in the description of the flow velocity determining operation of the blood BL of the present embodiment, which will be described below.

In the above, the function and the configuration of the flow velocity determining apparatus 10 of the present embodiment have been described.

<Flow Velocity Determining Operation of First Embodiment>

Next, the flow velocity determining operation of the blood BL by the flow velocity determining apparatus 10 of the present embodiment will be described mainly with reference to FIGS. 3A and 3B.

First, in a case in which a measurer presses a measurement start button (not shown) after making the measurement preparation (device setting, and the like) of the flow velocity determining apparatus 10, the flow velocity determining operation is started. This operation is performed by the control unit 40 in accordance with the measurement program CP. As a whole, first, the irradiating unit 20 emits the irradiation light L1. The irradiation light L1 is reflected by the red blood cells BC contained in the blood BL to become the reflected light L2. In this case, the reflected light L2 is scattered due to the shape of the red blood cell BC, and this scattering distribution has a regularity due to the flow velocity of the blood BL (see FIGS. 3A to 3C).

Next, the first detecting unit 32 and the second detecting unit 34 each detect the reflected light L2, and sequentially transmit the detection signals of the detected reflected light L2 to the control unit 40.

Next, the control unit 40, which receives the detection signals transmitted from the first detecting unit 32 and the second detecting unit 34, compares the detection signals of the light amount (first light amount) of the reflected light L2 detected by the first detecting unit 32 with the detection signals of the light amount (second light amount) of the reflected light L2 detected by the second detecting unit 34 to determine the flow velocity of the blood BL.

Figure 3A:
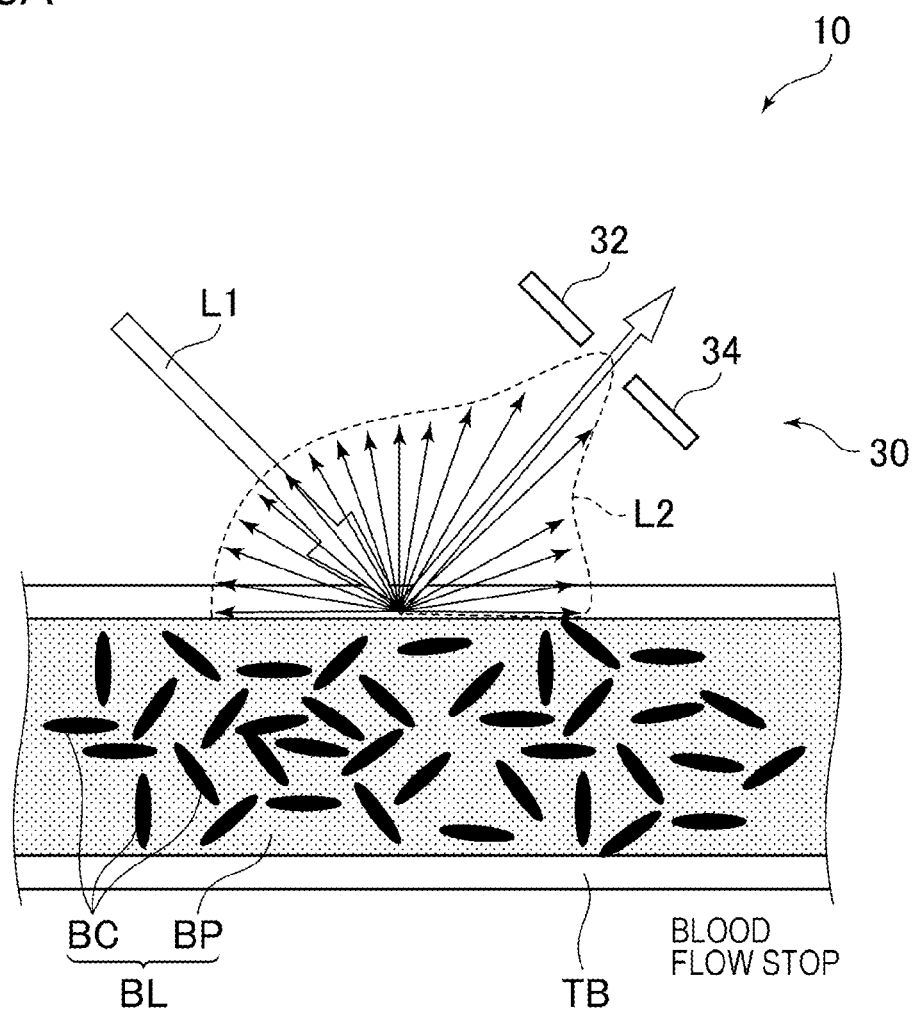
FIG. 3A is a diagram at the time of a blood flow velocity determining operation by the flow velocity determining apparatus of the first embodiment, and is a schematic diagram showing a distribution of reflected light in a case in which blood does not flow.

Here, FIG. 3A is a diagram at the time of the flow velocity determining operation of the blood BL, and is a schematic diagram showing the distribution of the reflected light L2 in a case in which the blood BL does not flow. FIG. 3B is a schematic diagram showing the distribution of the reflected light L2 in a case in which the blood BL flows in a forward direction. FIG. 3C is a schematic diagram showing the distribution of the reflected light L2 in a case in which the blood BL flows in an opposite direction.

As described above, the blood BL is a liquid mixture in which a blood cell (solid) portion substantially formed of the red blood cells BC and the blood plasma BP substantially formed of water are mixed. It is known that red blood cell BC has a disk-like shape having a concave center portion. It is also known that in a case in which the solid having such a shape flows together with the liquid, the respective red blood cells BC face in the same direction (have a similarly inclined posture) (see FIGS. 3B and 3C). The flow velocity determining apparatus 10 of the present embodiment determines the blood flow direction by using this phenomenon.

Figure 2:
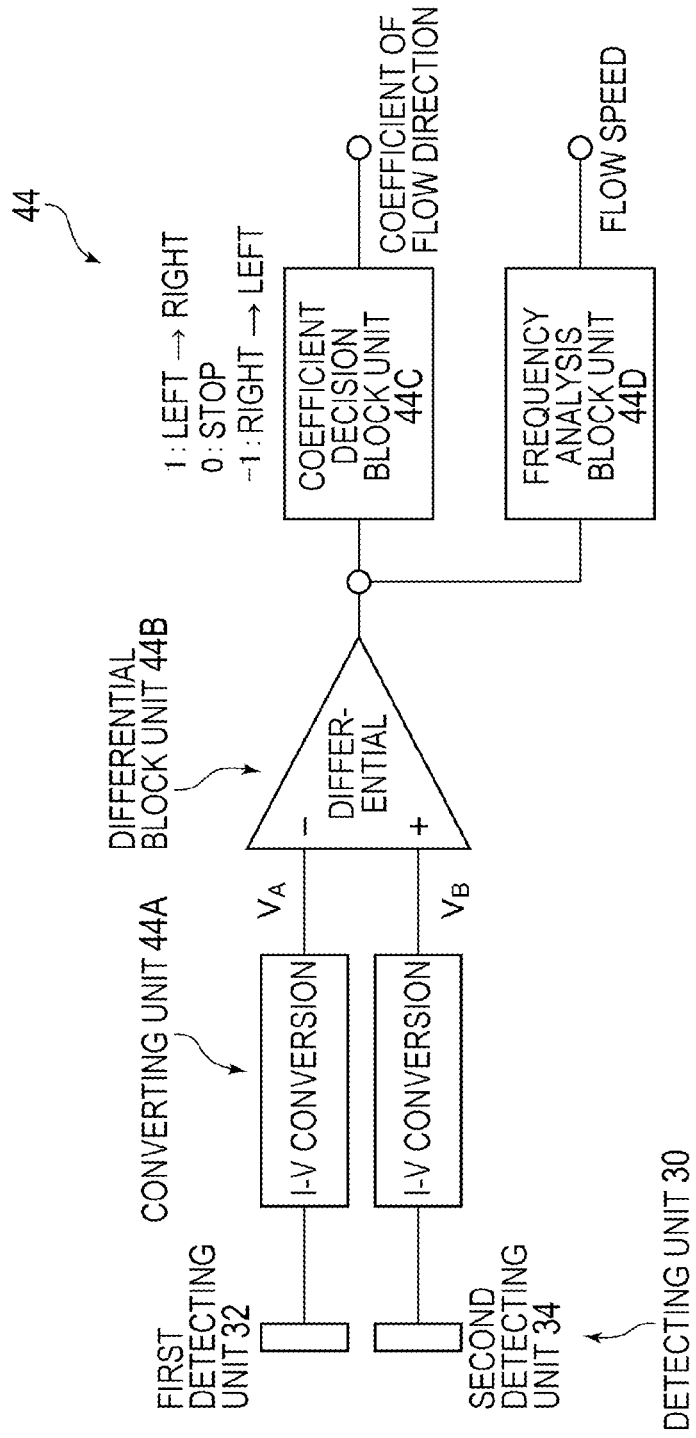
FIG. 2 is a processing block diagram of a signal processing unit configuring the flow velocity determining apparatus of the first embodiment.

Here, FIG. 2 is a processing block diagram of a signal processing unit 44 included in the control unit 40 of the flow velocity determining apparatus 10 of the present embodiment. The signal processing unit 44 includes a converting unit 44A, a differential block unit 44B, a coefficient decision block unit 44C, and a frequency analysis block unit 44D. The signal processing unit 44 performs I-V conversion of the detection signals from the first detecting unit 32 and the second detecting unit 34 by the converting unit 44A (converted to a voltage $V_A$ and a voltage $V_B$, respectively), and converts the voltage $V_A$ and the voltage $V_B$ into $V_{diff}=V_B-V_A$ by the differential block unit 44B to which the voltage $V_A$ and the voltage $V_B$ are input. The coefficient decision block unit 44C determines that the blood flow direction is the forward direction (first direction, blood flow direction of FIG. 3B) in a case in which $V_{diff}$ is 1 in the following (conditional expression 1), determines that the blood flow direction is the opposite direction (second direction, blood flow direction of FIG. 3C) in a case in which $V_{diff}$ is −1 in the following (conditional expression 1), and determines that the blood flow is stopped (the blood BL does not flow, see FIG. 3A) in a case in which $V_{diff}$ is 0 in the following (conditional expression 1). The coefficient decision block unit 44C determines the size of $V_{diff}$ and decides the coefficient in accordance with the size of $V_{diff}$.

$$-1: V_{diff} < -|\alpha|$$

$$0: V_{diff} \le |\alpha|$$

$$1: V_{diff} > |\alpha| \quad \text{(Conditional Expression 1)}$$

Here, α is a set fixed number.

Specifically, the first detecting unit 32 and the second detecting unit 34 are disposed at positions in which the respective detection outputs are equal as a result in the state in which the blood BL does not flow (FIG. 3A).

Figure 3B:
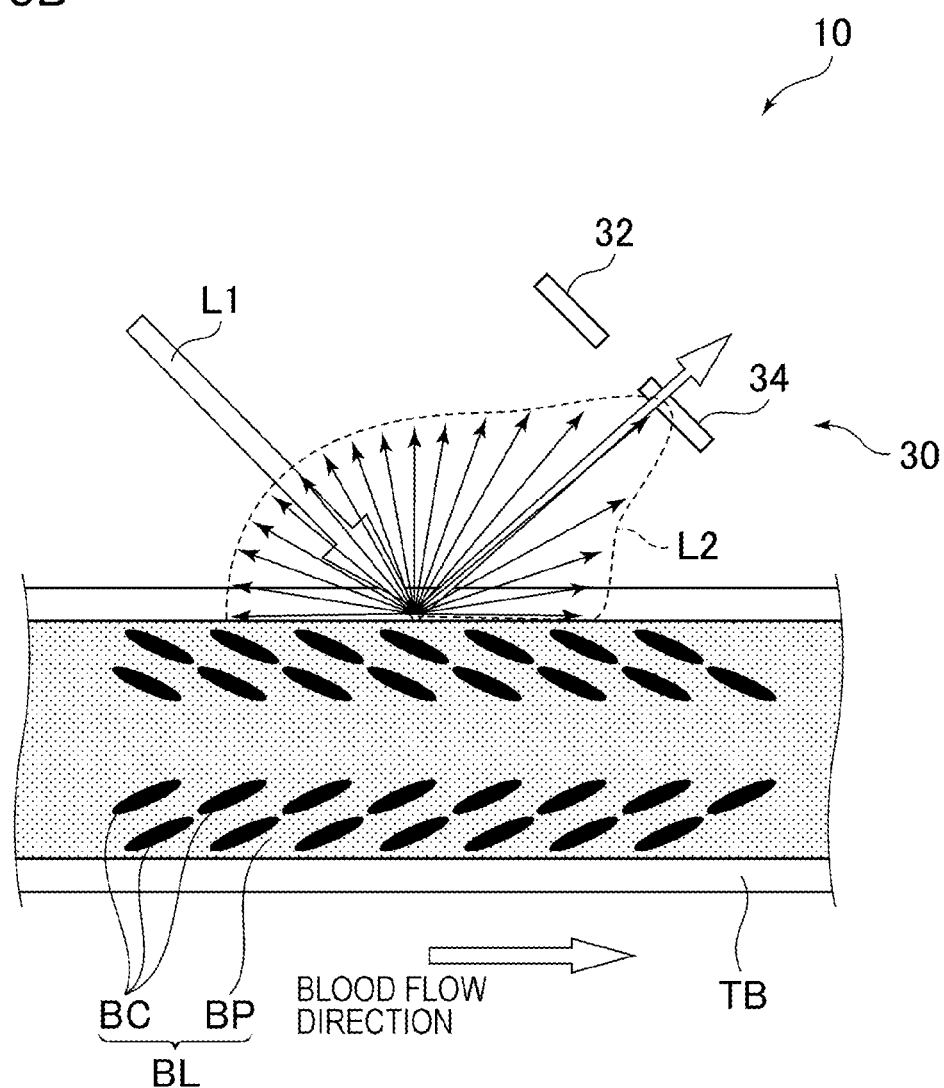
FIG. 3B is a diagram at the time of the blood flow velocity determining operation by the flow velocity determining apparatus of the first embodiment, and is a schematic diagram showing a distribution of reflected light in a case in which the blood flows in a forward direction.
Figure 3C:
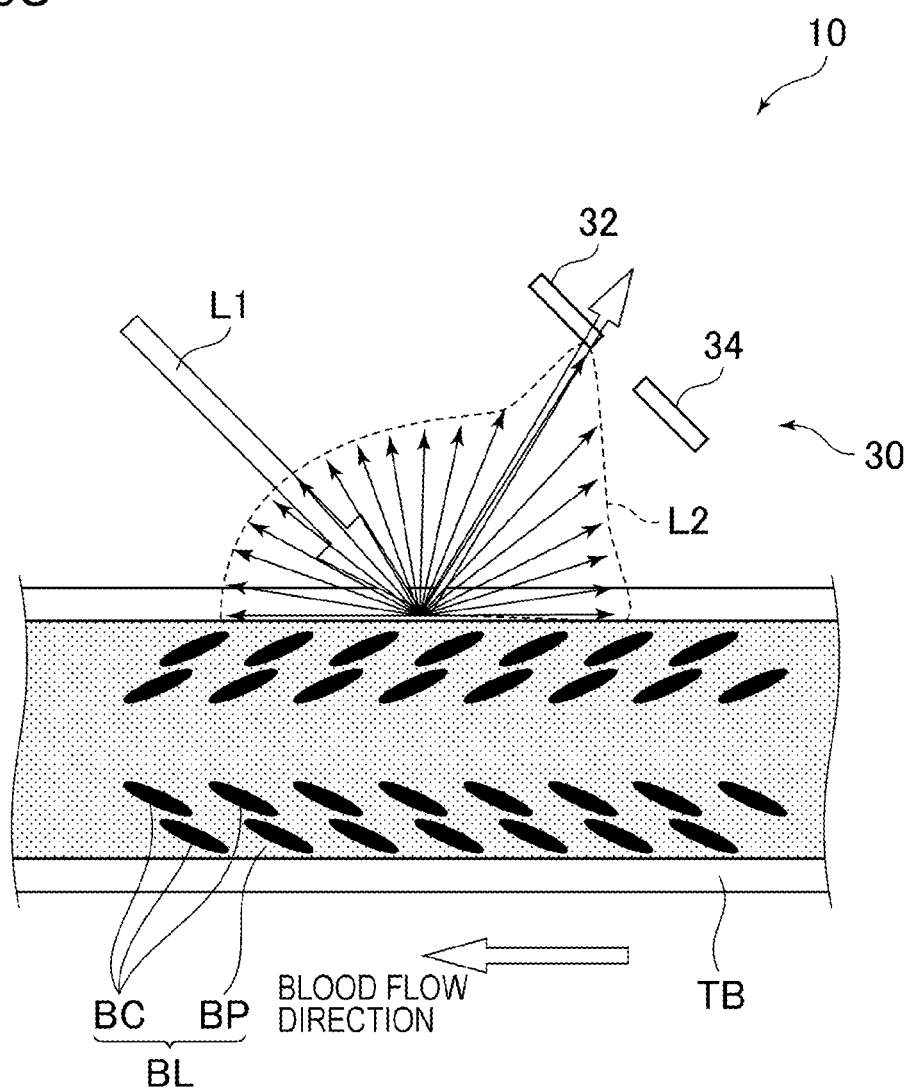
FIG. 3C is a diagram at the time of the blood flow velocity determining operation by the flow velocity determining apparatus of the first embodiment, and is a schematic diagram showing a distribution of reflected light in a case in which the blood flows in an opposite direction.

In the state in which the blood BL flows in the forward direction (see FIG. 3B), the red blood cells BC are oriented as shown in FIG. 3B, and the reflected light L2 is reflected as a mass inclined clockwise with respect to the case of FIG. 3A. Along with this, the detection intensity of the reflected light L2 incident on the first detecting unit 32 is decreased and the detection intensity of the reflected light L2 incident on the second detecting unit 34 is increased as compared with the state of FIG. 3A.

Further, in the case of FIG. 3C, that is, in a case in which the blood flow direction is opposite to that of FIG. 3B, the detection intensity of the reflected light L2 incident on the first detecting unit 32 is increased and the detection intensity of the reflected light L2 incident on the second detecting unit 34 is decreased as compared with the state of FIG. 3A.

Figure 4:
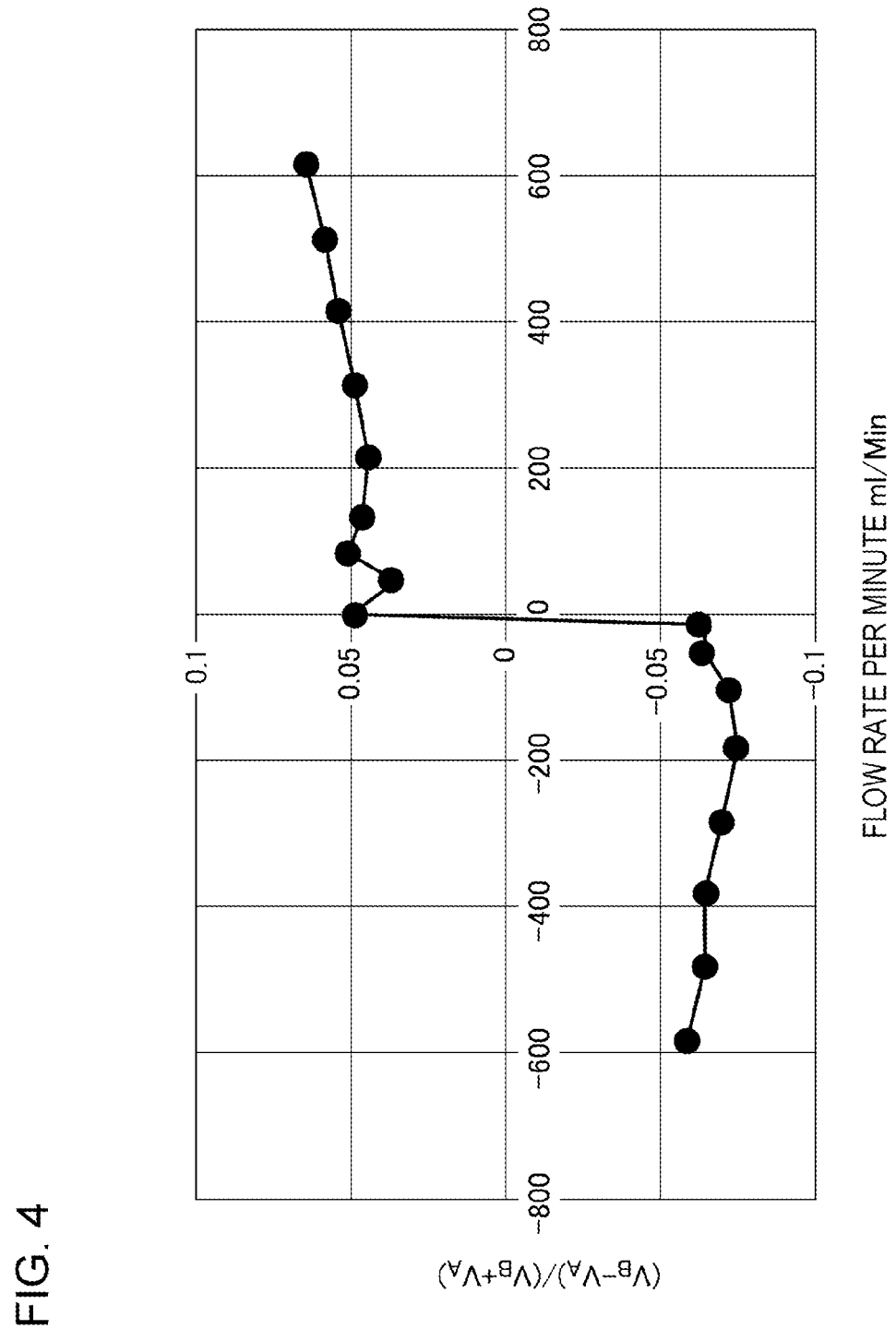
FIG. 4 is a graph showing a measurement result of the blood flow velocity determining operation by the flow velocity determining apparatus of the first embodiment.

FIG. 4 is a graph showing a measurement result of the flow velocity determining operation of the blood BL by the flow velocity determining apparatus 10 of the present embodiment. In this graph, the horizontal axis represents the flow rate per minute ml/Min. and the vertical axis represents $V_{diff}/(V_B+V_A)$. The value sharply reverses at the flow rate of 0 (flow velocity 0) per minute. That is, the coefficient α described above can be used as a coefficient indicating the flow direction.

Here, in a case in which the flow rate per minute ml/Min. of the horizontal axis is positive, that is, in a case of $V_{diff}$ ($=V_B-V_A$)>0, it is determined that the flow direction of the blood BL is the forward direction. On the other hand, in a case in which the flow rate per minute ml/Min. of the horizontal axis is negative, that is, in a case of $V_{diff}$ ($=V_B-V_A$)<0, it is determined that the flow direction of the blood BL is the opposite direction. Further, in a case of $V_{diff} \le |\alpha|$, that is, in a case in which the difference between $V_B$ and $V_A$ is equal to or smaller than a determined difference α (an example of the reference difference), it is determined that the blood BL does not flow.

The frequency analysis block unit 44D determines the velocity of the blood BL. The reason why the signal processing unit 44 can make the above determination is that the irradiating unit 20 is the laser light source, and the Doppler-shifted light L2 due to the flow of the blood BL is incident on the first detecting unit 32 and the second detecting unit 34, so the output of the Doppler-shifted light L2 is calculated (calculation such as obtaining the power spectrum by FFT and obtaining the average frequency). Specific description is as follows.

Figure 5:
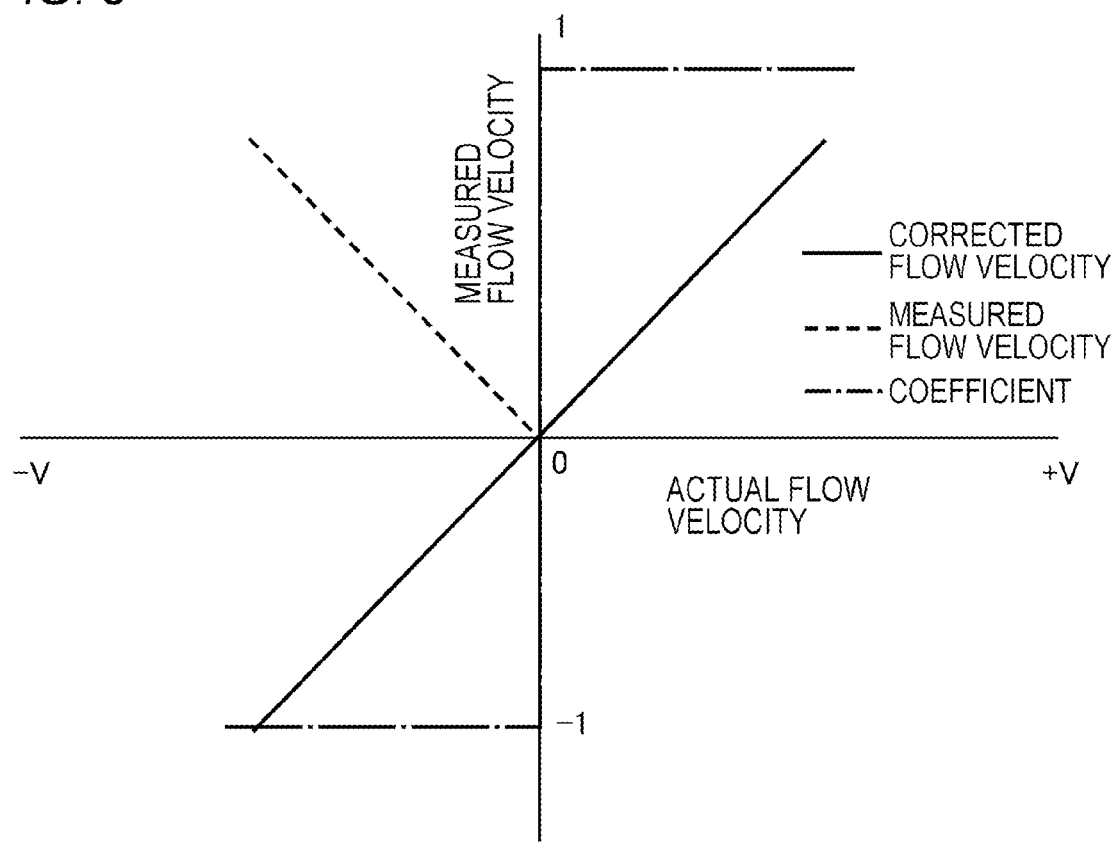
FIG. 5 is a graph showing a blood flow velocity obtained by correction with the flow velocity determining apparatus of the first embodiment.

FIG. 5 is a graph showing the blood flow velocity obtained by correction with the measurement program CP of the flow velocity determining apparatus 10 of the present embodiment. As shown in the graph of FIG. 4, the velocity of the blood BL can be obtained by multiplying the obtained flow rate per minute by the coefficient α of the (conditional expression 1). Further, the blood flow rate can be obtained by calculation using parameters such as the blood velocity and the size of the cross-sectional area of the blood circuit (cross-sectional area of tube TB).

As described above, with the flow velocity determining apparatus 10 of the present embodiment, the flow velocity of the blood BL that flows through the tube TB can be determined with a simple configuration.

In the above, the flow velocity determining operation of the present embodiment has been described. Further, in the above, the first embodiment has been described.

Second Embodiment

Next, a second embodiment will be described with reference to FIGS. 6 and 7. In the description of the present embodiment, in a case in which the same components as the components of the first embodiment are used as the components of the present embodiment, the same names, symbols, and the like are used. Hereinafter, portions different from those of the first embodiment of the present embodiment will be described.

Figure 6:
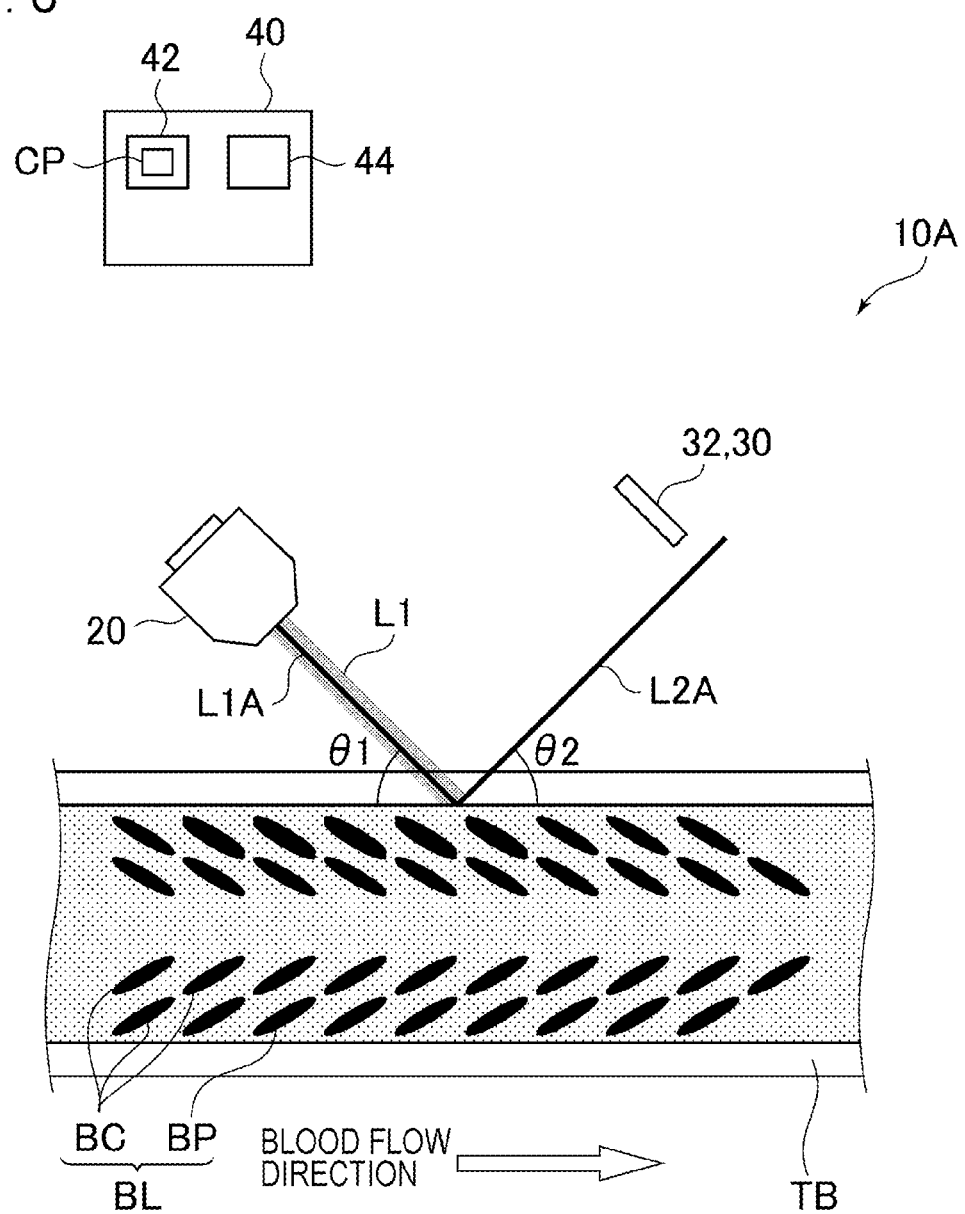
FIG. 6 is a diagram showing a flow velocity determining apparatus of a second embodiment, and is a vertical cross-sectional view in a state in which the flow velocity determining apparatus is set in a tube.

FIG. 6 is a diagram showing a flow velocity determining apparatus 10A of the present embodiment, and is a vertical cross-sectional view in a state in which the flow velocity determining apparatus 10A is set in the tube TB.

The flow velocity determining apparatus 10A of the present embodiment is different from the flow velocity determining apparatus 10 of the first embodiment (see FIG. 1A) only in that the detecting unit 30 is configured by only the first detecting unit 32. That is, in the present embodiment, the detecting unit 30 is disposed on any one side of both sides of the optical axis L2A when seen in a plan view of the imaginary plane (not shown) including the optical axis L1A and the optical axis L2A.

Figure 7:
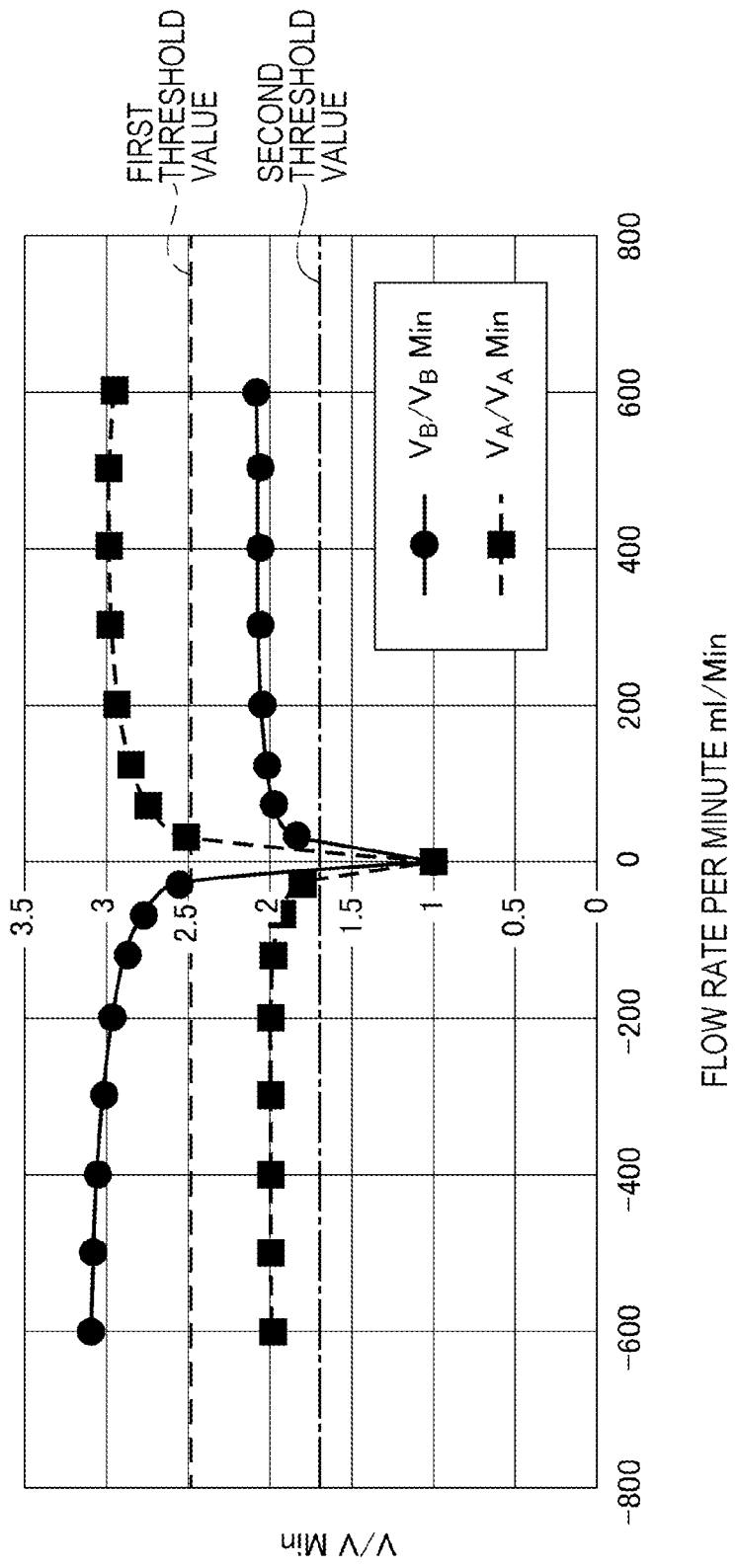
FIG. 7 is a graph used for determining a flow velocity in the blood flow velocity determining operation by the flow velocity determining apparatus of the second embodiment.

Here, FIG. 7 is a graph used for determining the flow velocity of the blood BL by the flow velocity determining apparatus 10A of the present embodiment, and a graph obtained by normalizing the graph of FIG. 4 of the first embodiment by a voltage $V_{min}$ in a case of the flow rate of 0 per minute. As shown in the graph of FIG. 7, the standard values $V_A/V_{min}$ and $V_B/V_{min}$ of each measured value change significantly at the flow rate of 0 (a state in which the blood BL does not flow). Therefore, for example, by setting the broken lines in FIG. 7 as threshold values, the flow direction and the flow rate of the blood BL can be determined by only one of the first detecting unit 32 and the second detecting unit 34.

Further, by setting the broken lines in FIG. 7 as a first threshold value (an example of a first reference amount) and a second threshold value (an example of a second reference amount), the state in which the blood BL flows in the forward direction, the state in which the blood BL is stopped, and the state in which the blood BL flows in the opposite direction can be determined as follows. Specifically, in a case in which the light amount detected by the detecting unit 30 (in this case, the first detecting unit 32) is larger than the first threshold value, it is determined that the flow direction of the blood BL is the forward direction. Further, in a case in which the light amount detected by the detecting unit 30 (in this case, the first detecting unit 32) is smaller than the first threshold value and larger than the second threshold value, it is determined that the flow direction of the blood BL is the opposite direction. Further, in a case in which the light amount detected by the detecting unit 30 (in this case, the first detecting unit 32) is equal to or smaller than the second threshold value, it is determined that the blood BL is stopped (does not flow). In addition, the flow rate per minute can be determined from the values in the graph of FIG. 7.

As described above, in the present embodiment, the same effects as those of the first embodiment are obtained with simple configuration (configuration including only one of the first detecting unit 32 and the second detecting unit 34) as compared with the first embodiment (see FIG. 1A).

In the above, the second embodiment has been described.

Third Embodiment

Next, a third embodiment will be described with reference to FIGS. 8 and 9A to 9C. In the description of the present embodiment, in a case in which the same components as the components of the first embodiment are used as the components of the present embodiment, the same names, symbols, and the like are used. Hereinafter, portions different from those of the first embodiment of the present embodiment will be described.

FIG. 8 is a diagram showing a flow velocity determining apparatus 10C of the present embodiment, and is a vertical cross-sectional view in a state in which the flow velocity determining apparatus 10C is set in the tube TB.

The flow velocity determining apparatus 10C of the present embodiment is different from the flow velocity determining apparatus 10 of the first embodiment (see FIG. 1A), and an irradiating unit 20C is disposed such that the irradiation light L1 emitted by the irradiating unit 20C itself has the optical axis L1A in a vertical direction (radial direction of the tube TB) with respect to the tube TB, that is, the blood BL that flows through the tube TB. Further, the light L1 emitted by the irradiating unit 20C is not coherent light, but is light having a spread while having the optical axis L1A in the radial direction of the tube TB. Further, in the present embodiment, the first detecting unit 32 and the second detecting unit 33 are disposed on both sides of the irradiating unit 20C (both sides of the optical axis L1A).

The differences between the present embodiment and the first embodiment are as above.

Figure 9A:
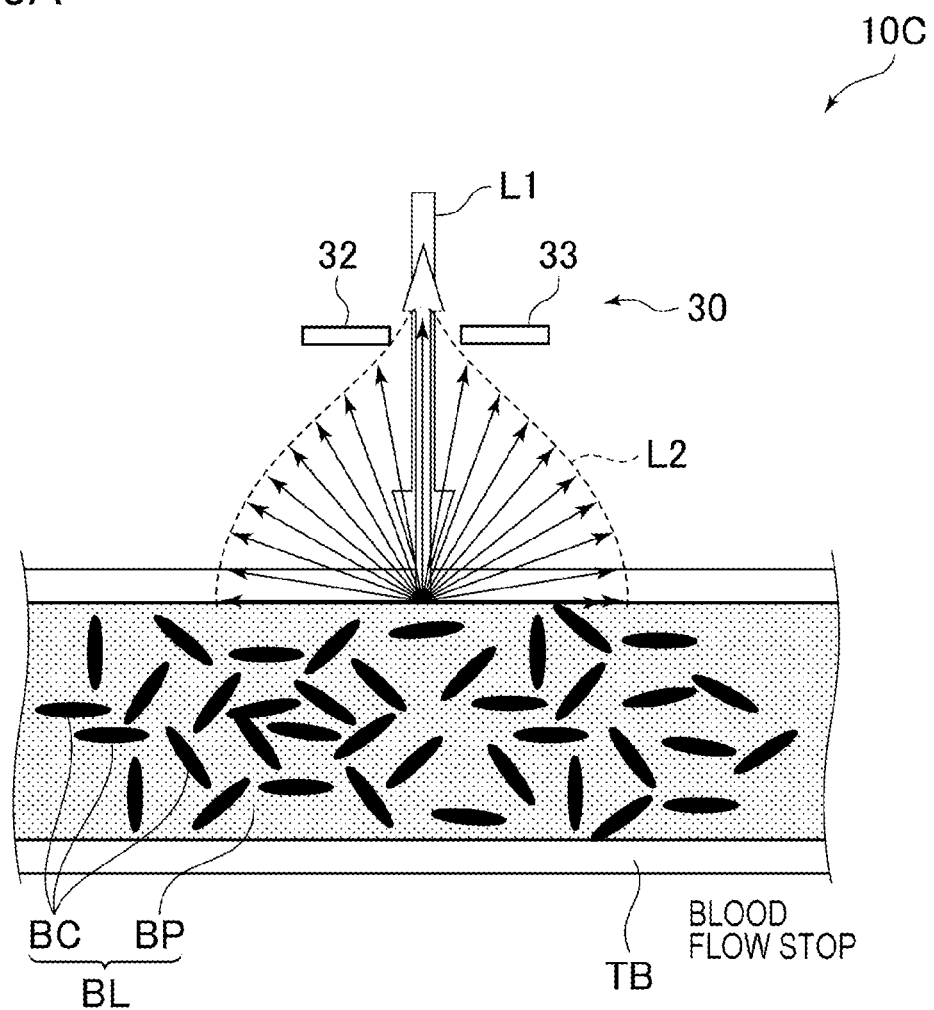
FIG. 9A is a diagram at the time of a blood flow velocity determining operation by the flow velocity determining apparatus of the third embodiment, and is a schematic diagram showing a distribution of reflected light in a case in which blood does not flow.
Figure 9B:
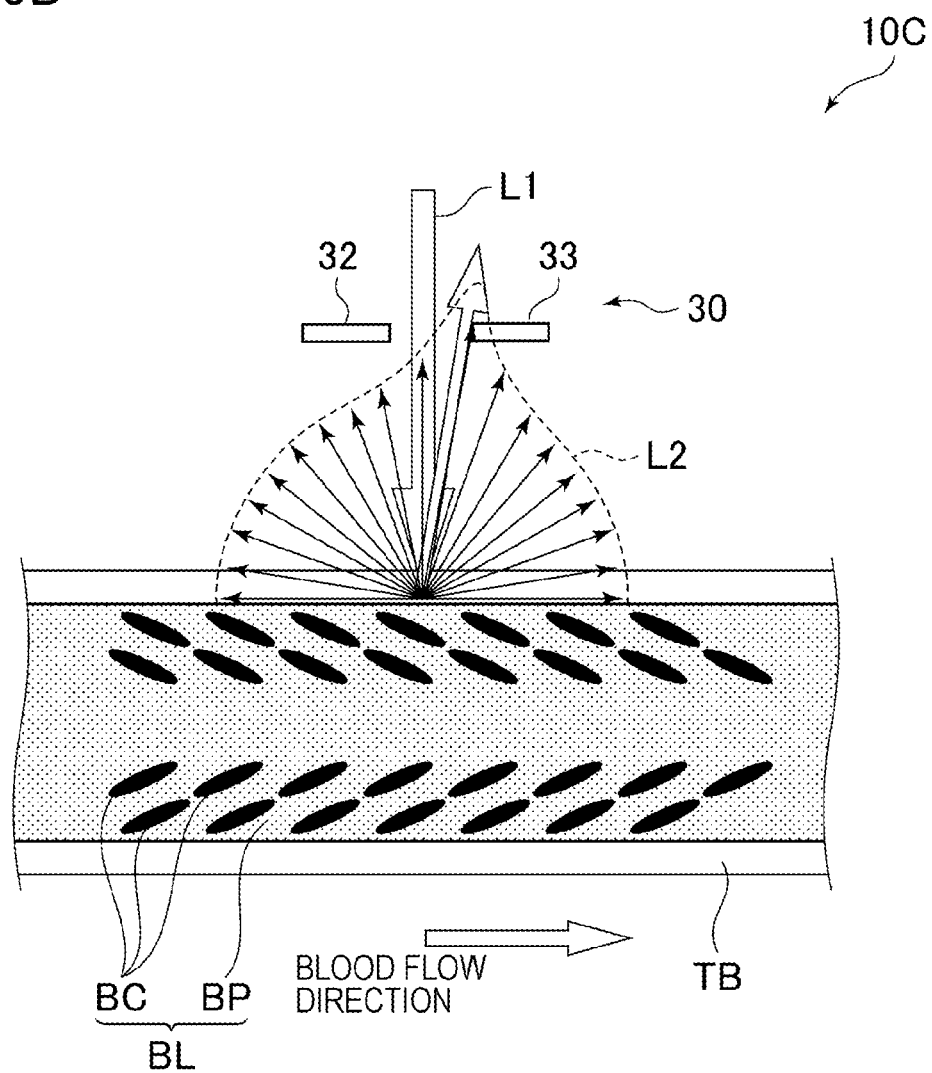
FIG. 9B is a diagram at the time of the blood flow velocity determining operation by the flow velocity determining apparatus of the third embodiment, and is a schematic diagram showing a distribution of reflected light in a case in which the blood flows in a forward direction.
Figure 9C:
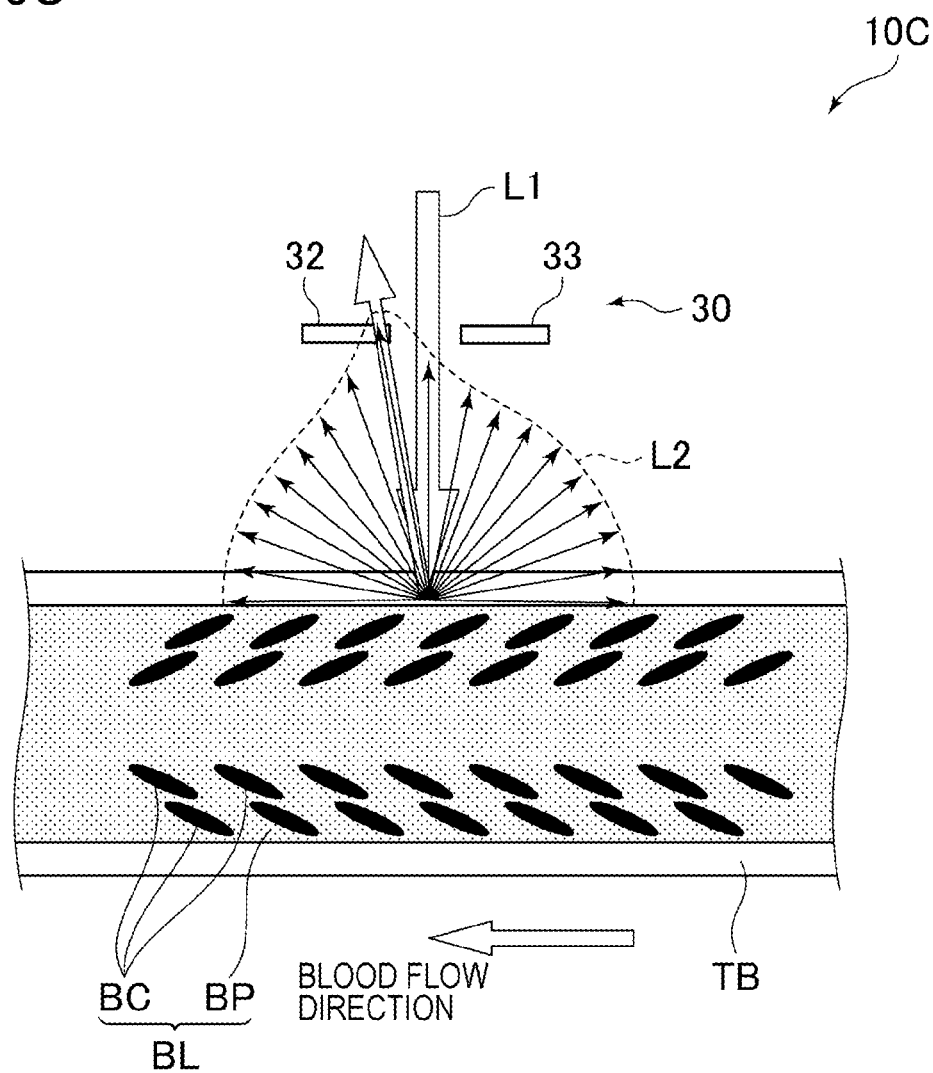
FIG. 9C is a diagram at the time of the blood flow velocity determining operation by the flow velocity determining apparatus of the third embodiment, and is a schematic diagram showing a distribution of reflected light in a case in which the blood flows in an opposite direction.

Here, FIG. 9A is a diagram at the time of the flow velocity determining operation of the blood BL of the flow velocity determining apparatus 10C of the present embodiment, and is a schematic diagram showing the distribution of the reflected light L2 in a case in which the blood BL does not flow. Further, FIG. 9B is a schematic diagram showing the distribution of the reflected light L2 in a case in which the blood BL flows in the forward direction. Further, FIG. 9C is a schematic diagram showing the distribution of the reflected light L2 in a case in which the blood BL flows in the opposite direction.

Although the configuration of the present embodiment is different from that of the first embodiment, the scattering distribution of the blood BL due to the flow velocity (see FIGS. 9A to 9C) has a regularity that has the same tendency as the scattering distribution of the first embodiment (see FIGS. 3A to 3C).

As described above, in the present embodiment, the same effects as those of the first embodiment are obtained.

As described above, the first to third embodiments have been described as an example of the present invention, but the present invention is not limited thereto. The technical scope of the present invention also includes, for example, the following modes (modification examples).

Figure 10:
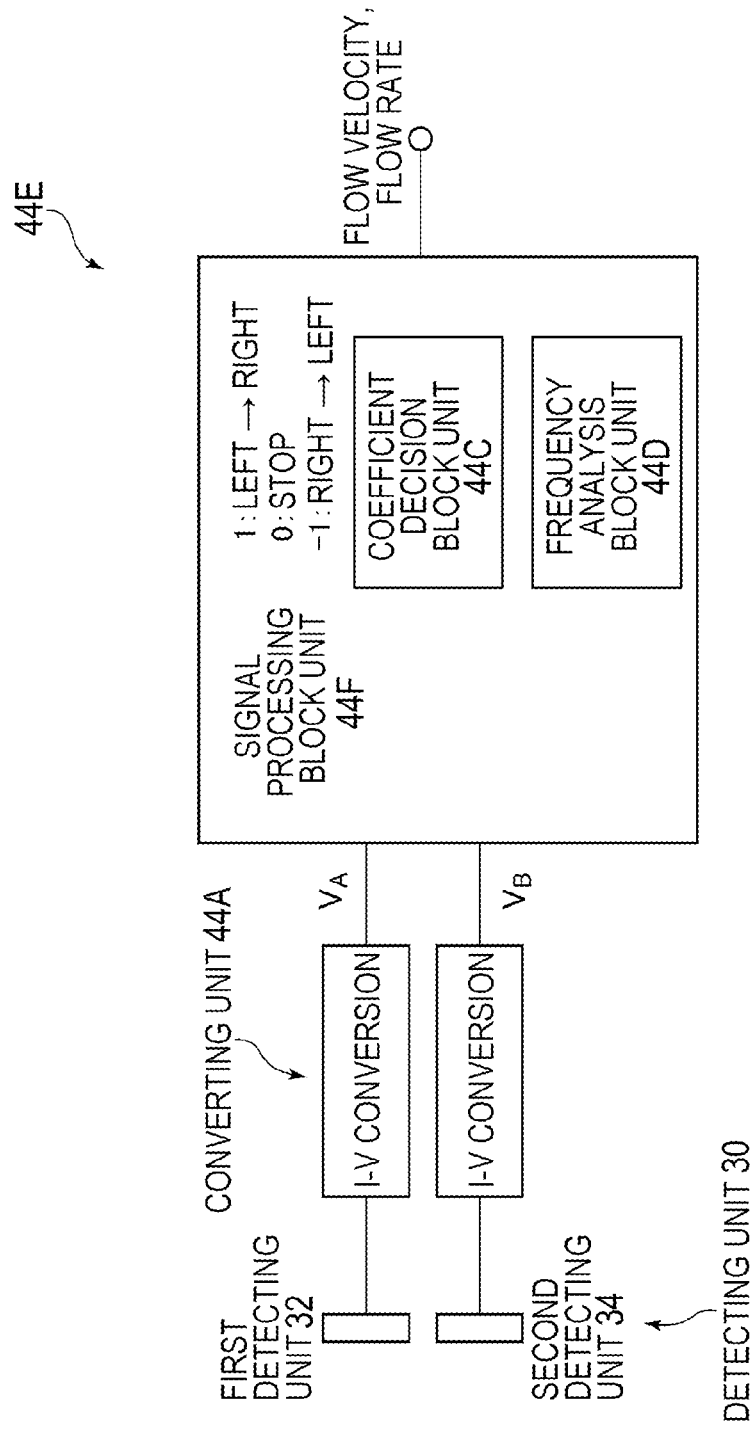
FIG. 10 is a processing block diagram of a signal processing unit of a first modification example.

For example, in the first embodiment, the I-V converted detection signals are differentially processed (see FIG. 2), but the I-V converted detection signals may be directly processed by a signal processing block unit 44F of a signal processing unit 44E of a first modification example shown in FIG. 10 without differential processing.

Figure 11:
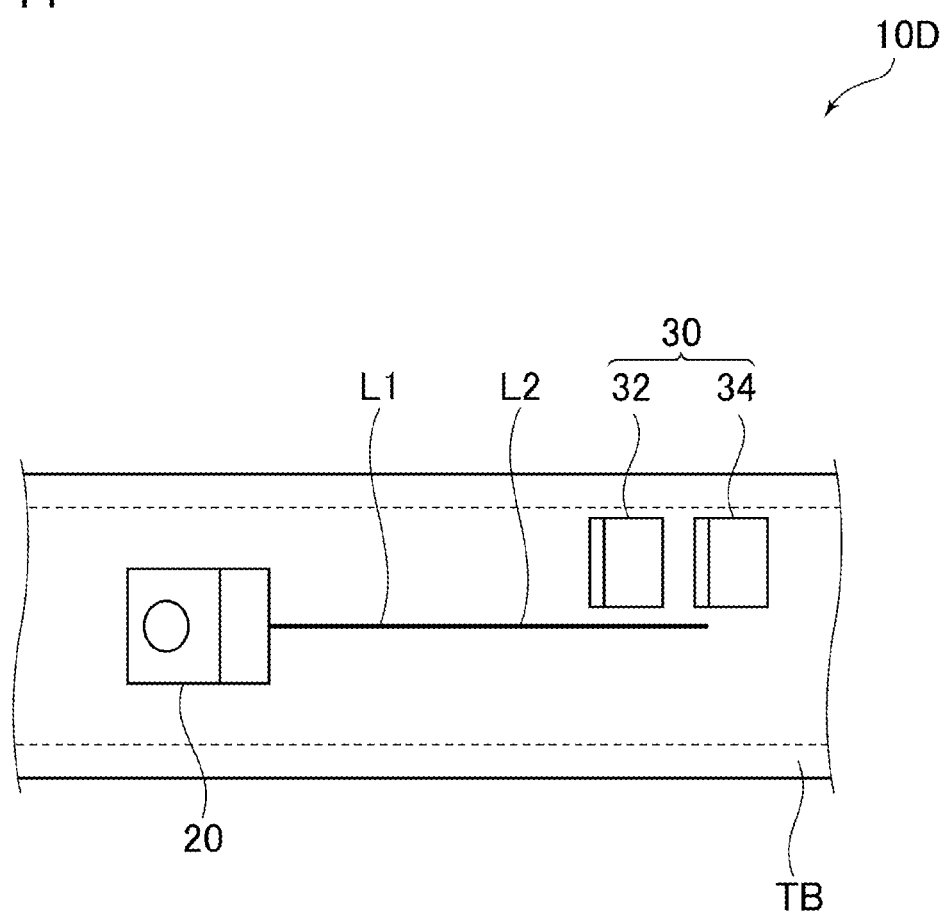
FIG. 11 is a top view showing a disposition example of a flow velocity determining apparatus and a tube of a second modification example.

Further, as in a flow velocity determining apparatus 10D of a second modification example shown in FIG. 11, the first detecting unit 32 and the second detecting unit 34 (detecting unit 30) may be disposed to be offset in a circumferential direction of the tube TB from the position of the detecting unit 30 of the first embodiment (see FIG. 1B).

Figure 12:
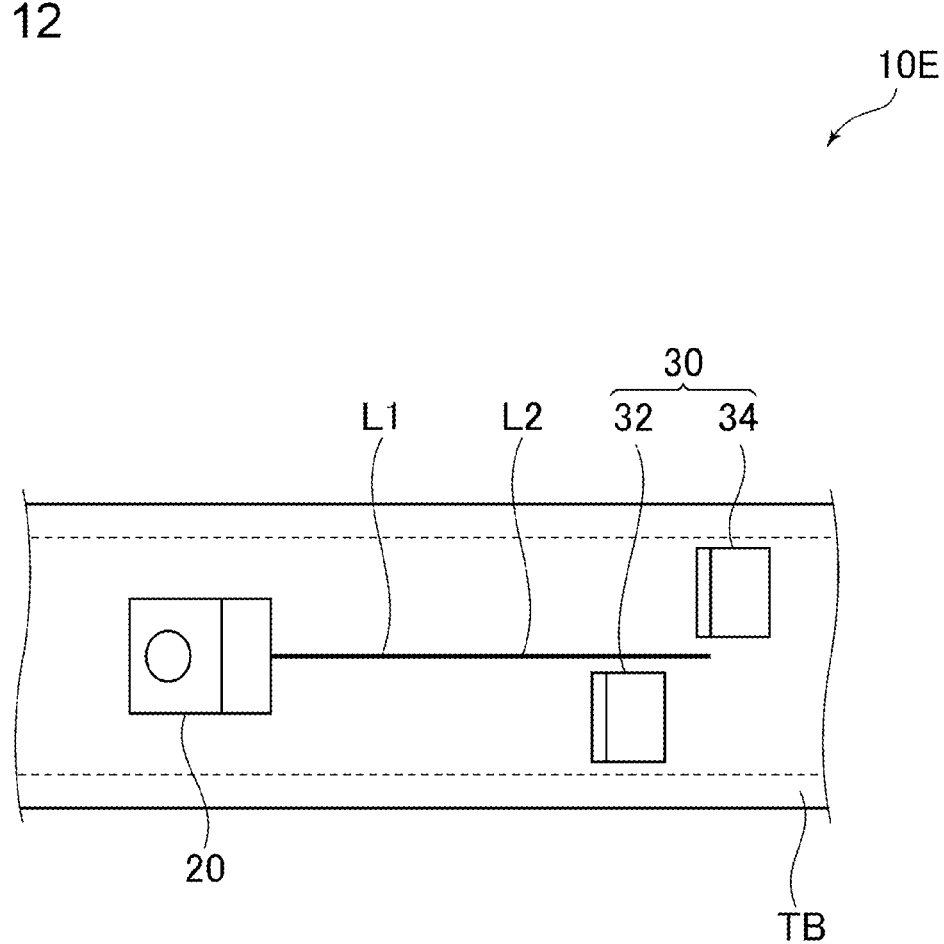
FIG. 12 is a top view showing a disposition example of a flow velocity determining apparatus and a tube of a third modification example.

Further, as in a flow velocity determining apparatus 10E of a third modification example shown in FIG. 12, the first detecting unit 32 and the second detecting unit 34 (detecting unit 30) may be disposed to be offset in different directions in the circumferential direction of the tube TB from the position of the detecting unit 30 of the first embodiment (see FIG. 1B).

Figure 13:
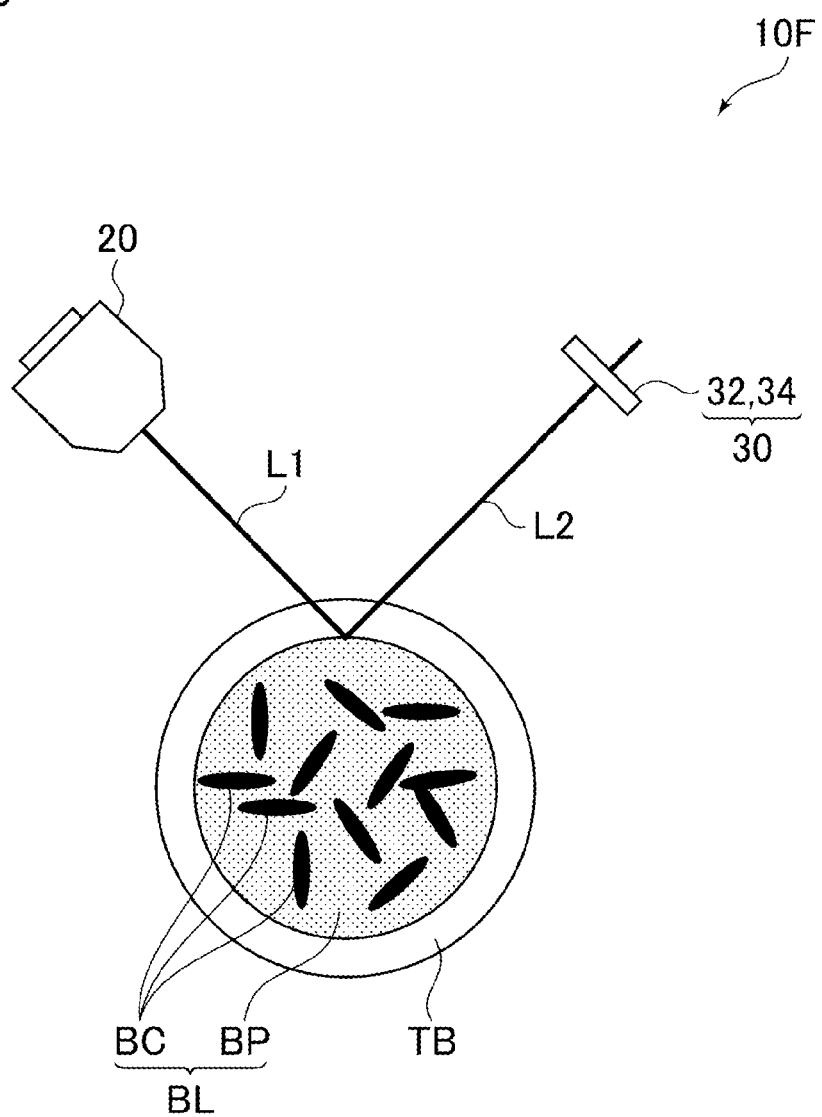
FIG. 13 is a horizontal cross-sectional view showing a disposition example of a flow velocity determining apparatus and a tube of a fourth modification example.

Further, as in a flow velocity determining apparatus 10F of a fourth modification example shown in FIG. 13, each of the irradiating unit 20 and the detecting unit 30 may be disposed at a position inclined with respect to the radial direction of the tube TB when seen in a horizontal cross-sectional view of the tube TB.

Further, in the first and third embodiments, it has been described that the first detecting unit 32 and the second detecting unit 34 are disposed so as to interpose the optical axis L2A therebetween (see FIGS. 1A and 8). However, one detecting unit (any one of the first detecting unit 32 and the second detecting unit 34) may be disposed across the optical axis L2A (not shown). Further, the detecting unit 30 (see FIG. 6) of the second embodiment may be disposed across the optical axis L2A (not shown). In these cases, the detecting unit disposed across the optical axis L2A need only be, for example, a PSD or a multi-segment photodetector in order to be able to detect a change in the intensity distribution of the reflected light L2.

Further, in the present specification, for convenience, each embodiment has been described individually, but for example, the components of other embodiments may be incorporated into any one of the embodiments. For example, the flow velocity may be determined by the modification example with the idea of the second embodiment (FIG. 7) by omitting one detecting unit 30 (any one of the first detecting unit 32 and the second detecting unit 33) of the flow velocity determining apparatus 10C of the third embodiment (see FIG. 8).

Further, in each embodiment, the blood BL has been described as an example of the liquid mixture. However, the target to be measured by the flow velocity determining apparatus 10 or the like of each embodiment may not be blood BL as long as the liquid mixture contains a non-spherical solid. For example, another example of the liquid mixture may be a liquid mixture that contains a magnetic fluid, microcapsules, or the like.

Further, the flow velocity determining apparatus 10 or the like of each embodiment determines the flow velocity of the blood BL, but it may be applied to the following applications. For example, it may be applied to an apparatus (not shown) that is installed in a blood flow circuit used for dialysis, an artificial heart-lung machine, or the like and measures the flow rate of the blood that flows through the blood flow circuit in a non-contact manner. Further, it may be applied to a blood flow regurgitation monitoring apparatus (not shown) that is installed in the blood flow circuit used for dialysis, the artificial heart-lung machine, or the like, detects blood flow regurgitation, and performs alarm and emergency operation.

The invention claimed is:

1. A flow velocity determining apparatus comprising:
an irradiating unit that emits irradiation light toward a liquid mixture which contains a non-spherical solid and a liquid and flows through a flow path;
a detecting unit that detects reflected light emitted by the irradiating unit and reflected by the liquid mixture flowing through the flow path, the detecting unit being disposed on at least one side of an optical axis of the reflected light when seen in a plan view of an imaginary plane including an optical axis of the irradiation light and the optical axis of the reflected light, the optical axis of the irradiation light and the optical axis of the reflected light being on a same line when viewed from a normal direction of a reflection surface at a reflection point, and an angle of the optical axis of the reflected light with respect to the flow path being $-\theta 1$ in a case in which an angle of the optical axis of the irradiation light with respect to the flow path is defined as an angle $\theta 1$; and
a determining unit that determines a flow velocity of the liquid mixture by using a light amount of the reflected light detected by the detecting unit,
wherein the detecting unit includes a first detecting unit disposed on one side of the optical axis of the reflected light and a second detecting unit disposed on an other side when seen in the plan view of the imaginary plane; and
the determining unit compares a first light amount of the reflected light detected by the first detecting unit with a second light amount of the reflected light detected by the second detecting unit to determine the flow velocity of the liquid mixture.

2. The flow velocity determining apparatus according to claim 1,
wherein the determining unit determines a flow direction of the liquid mixture as a first direction from one side of the flow path toward the other side of the flow path in a case in which the first light amount is larger than the second light amount and a difference between the first light amount and the second light amount is larger than a reference difference, and determines the flow direction of the liquid mixture as a second direction opposite to the first direction in a case in which the first light amount is smaller than the second light amount and the difference between the first light amount and the second light amount is larger than the reference difference.

3. The flow velocity determining apparatus according to claim 2,
wherein the determining unit determines that the liquid mixture does not flow in a case in which the difference between the first light amount and the second light amount is equal to or smaller than the reference difference.

4. The flow velocity determining apparatus according to claim 1,
wherein the liquid mixture is blood containing red blood cells as the solid.

* * * * *